(12) United States Patent
Ho et al.

(10) Patent No.: US 7,988,450 B2
(45) Date of Patent: Aug. 2, 2011

(54) DENTAL IMPRESSION TRAY AND METHOD OF USING THE SAME

(75) Inventors: Phillip Phung-I Ho, Santa Barbara, CA (US); Chung-Chieh Lee, Banciao (TW)

(73) Assignee: Phillip Phung-I HO, Santa Barbara, CA (US)

( * ) Notice: Subject to any disclaimer, the term of this patent is extended or adjusted under 35 U.S.C. 154(b) by 300 days.

(21) Appl. No.: 12/237,543

(22) Filed: Sep. 25, 2008

(65) Prior Publication Data

US 2010/0075279 A1    Mar. 25, 2010

(51) Int. Cl.
*A61C 9/00* (2006.01)
*A61C 19/04* (2006.01)
(52) U.S. Cl. .......................... 433/214; 433/73
(58) Field of Classification Search ................ 433/6, 73, 433/72, 75, 68, 69, 37, 215, 44, 55, 56; 33/513, 33/514
See application file for complete search history.

(56) References Cited

U.S. PATENT DOCUMENTS

| 4,689,010 A * | 8/1987 | Wolfe .......................... 433/38 |
| 6,029,668 A * | 2/2000 | Freed ...................... 128/207.17 |
| 7,601,000 B1 * | 10/2009 | Hammond et al. ............. 433/68 |

* cited by examiner

*Primary Examiner* — Cris L Rodriguez
*Assistant Examiner* — Heidi M Eide
(74) *Attorney, Agent, or Firm* — Rabin & Berdo, P.C.

(57) ABSTRACT

A dental impression tray has a base and a relator. The base has a biting portion and a handle. The biting portion is curved. The handle is formed on the biting portion and has an arc hole that is defined through the handle to receive impression material. The relator has a vertical bar and a horizontal bar. The relator is mounted in the arc hole and is fastened in the arc hole by impression material. The horizontal bar connects perpendicularly to the vertical bar. Therefore, the impression of the teeth to be crowned or veneered as well as the relation between the impression and the patient's face are obtained simultaneously.

3 Claims, 12 Drawing Sheets

DENTAL IMPRESSION TRAY AND METHOD OF USING THE SAME

BACKGROUND OF THE INVENTION

1. Field of Invention

The present invention relates to a dental impression tray, and more particularly to a dental impression tray that allows an operator to take an impression of a patient's dentition and simultaneously align the impression with the patient's face. This facilitates the fabrication of symmetrical, facially well-aligned, and aesthetic crowns, porcelain veneers, and/or bridges by the dental laboratory technician.

2. Description of the Related Art

When a patient requires a crown for at least one tooth, a dentist has to take an impression of the patient's dentition to produce a crown therefrom. When a patient requires a single incisor crown, the dental technician can produce the crown according to the other incisor. However, when two or more front teeth are involved, the dentist is required to not only take an impression of these teeth, but also align them with the patient's face using a device called Facial Plane Relator or FPR for short. The reason for this additional step of using the FPR is to ensure that the crowns fabricated by the dental technician are not slanted relative to the patient's face.

With reference to FIGS. 7A and 7B, FIG. 7A shows a conventional dental impression tray and FIG. 7B shows a conventional FPR (40).

With further reference to FIG. 8, a conventional impression tray comprises a base (30). The base (30) is curved corresponding to a human dentition and has an outer wall (31), an inner wall (33), a membrane (32) and a handle (34). The membrane (32) is formed between the outer wall (31) and the inner wall (33), is made up of meshes and is able to hold impression material such as silicon rubber or the like. The handle (34) is formed on the outer wall (31) opposite to the inner wall (33) to allow a dentist to hold the impression tray.

With further reference to FIGS. 9 and 10, the FPR (40) comprises an arch (44), a horizontal bar (42) and a vertical bar (41). Using the pupils of the eyes (50) as a guide, the horizontal bar (42) corresponds to a horizontal facial midline (91). Using the bridge of the nose (49B) and the philtrum (49A) as guides, the vertical bar (41) corresponds to a vertical facial midline (92). The arch (44) has an outer edge and an inner edge. The inner edge has multiple protrusions (45). The protrusions (45) radially protrude from the inner edge of the arch (44) and are arranged on the inner edge at intervals, the purpose of which is to help hold the impression material onto the arch (44). The horizontal bar (42) is formed tangentially on the outer edge of the arch (44) and has a clamp (43). The vertical bar (41) is secured by the clamp (43) of the horizontal bar (42) and holds the vertical bar (41) perpendicular to the horizontal bar (42).

When the conventional dental impression tray is used, a patient bites into the membrane (32) holding the impression material. After the impression materials have cured, the dental impression tray (30) is removed from a patent's mouth and a dental impression is obtained. The next step is to use the FPR (40) for determining the patient's dental-facial alignment. The protrusions (45) are applied with liberal amounts of impression materials for the patient to bite. When the patient bites the FPR (40) just medial (48) to the protrusions (45), the vertical and the horizontal bars (41, 42) are adjusted to align respectively with the bridge of the nose (49B), the philtrum (49A), and the eyes (50), so that the vertical bar (41) is in parallel with the bridge of the nose (49B) as well as the philtrum (49A) and the horizontal bar (42) is in parallel with the eyes (50). After the impression material has cured, the FPR (40) is detached from the mouth to obtain the relationship between the patient's dentition and face. The dental laboratory technician then uses this completed FPR (40) to fabricate crowns or dental veneers to ensure that the patient does not end up with a crooked smile after the crowns or veneers are cemented in the patient's mouth.

The entire process involved the dentist having to take two separate and distinct steps in order to obtain the impression and the relation and the patient is required to bite the impression materials twice. Therefore, obtaining the impression and the relation doubles both the dentist and the patient's time and cost as well as raising the discomfort level of the patient.

With reference to FIG. 11, an another FPR comprises a bitten sheet (51), an outer wall (52), a connecting bar (53), a horizontal bar (54) and a vertical bar (55). The bitten sheet (51) holds impression material and allows a patient to bite into the impression material. The outer wall (52) is formed on a side of the bitten sheet (51). An end of the connecting bar (53) is formed integrally on and protrudes from the outer wall (52). A central part of the horizontal bar (54) integrally connects perpendicularly with another end of the connecting bar (53) to align with patient's face horizontally. An end of the vertical bar (55) connects integrally with and protrudes upward from the central part of the horizontal bar (54) and is perpendicular to the horizontal bar (54) and the connecting bar (53) to align with patient's nose.

However, all elements of the another FPR are formed integrally, so the horizontal bar (54) and the vertical bar (55) both cannot be adjust. Therefore, the horizontal bar (54) and the vertical bar (55) cannot obtain an accurate relationship between the patient's dentition and face.

The present invention combines the function of an impression tray with a FPR such that only one step is required in obtaining both.

SUMMARY OF THE INVENTION

The primary objective of the present invention is to provide a dental impression tray that obtains an impression of a patient's dentition and aligns the impression with the patient's face simultaneously for the purpose of fabricating symmetrical and aesthetic crowns, bridges, or cosmetic veneers with reduced patient discomfort and time.

To achieve the objective, the dental impression tray in accordance with the present invention comprises a base and two bars. The two bars will serve as Facial Plane Relator (FPR) when removed from the base and assembled together to form a cross. The base has a biting portion and a handle. The biting portion is curved. The handle is formed on the biting portion and has an arc hole. The arc hole is defined through the handle to receive dental impression material such as silicone rubber. The FPR has a vertical bar and a horizontal bar. Assembling the FPR involves snapping the two bars together to form a cross. Once assembled, the vertical bar of the FPR is inserted into the arc hole and is held in place by the impression material. Therefore, the impression of the teeth and the relationship between the impression and the patient's face are obtained simultaneously. Before the impression material in the arc hole cures, the cross can be adjusted by hand.

Other objectives, advantages and novel features of the invention will become more apparent from the following detailed description when taken in conjunction with the accompanying drawings.

DETAILED DESCRIPTION OF THE INVENTION

Figure 1:
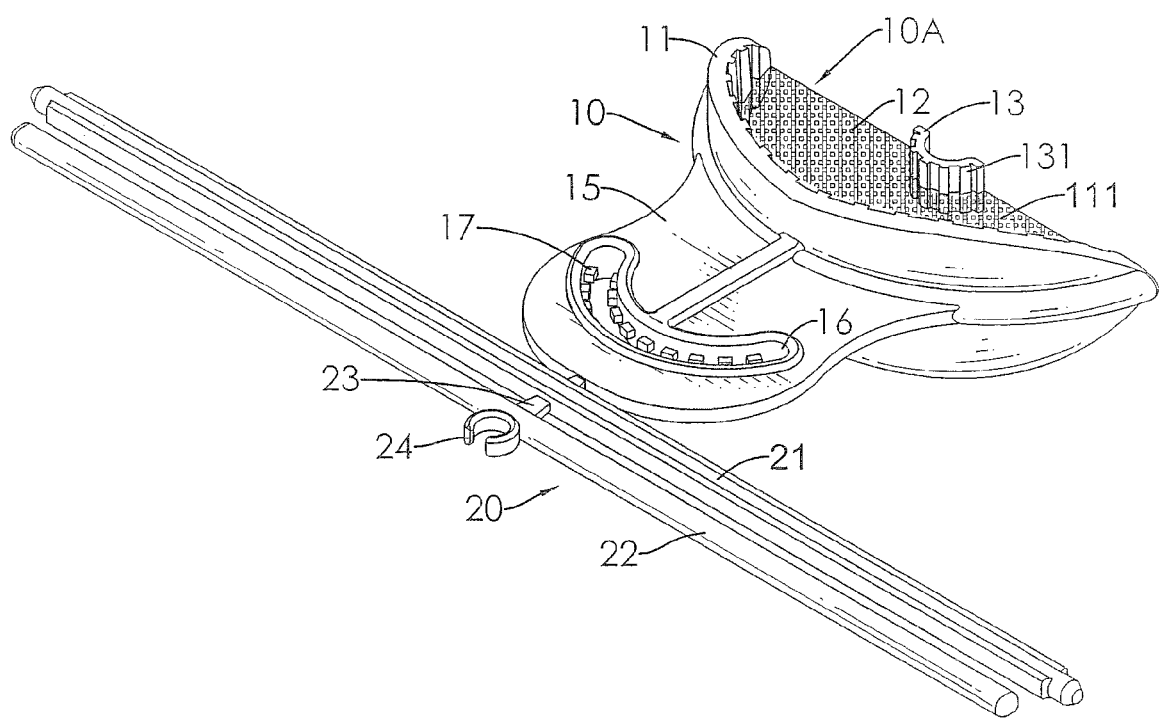
FIG. 1 is a perspective view of a dental impression tray in accordance with the present invention.
Figure 5:
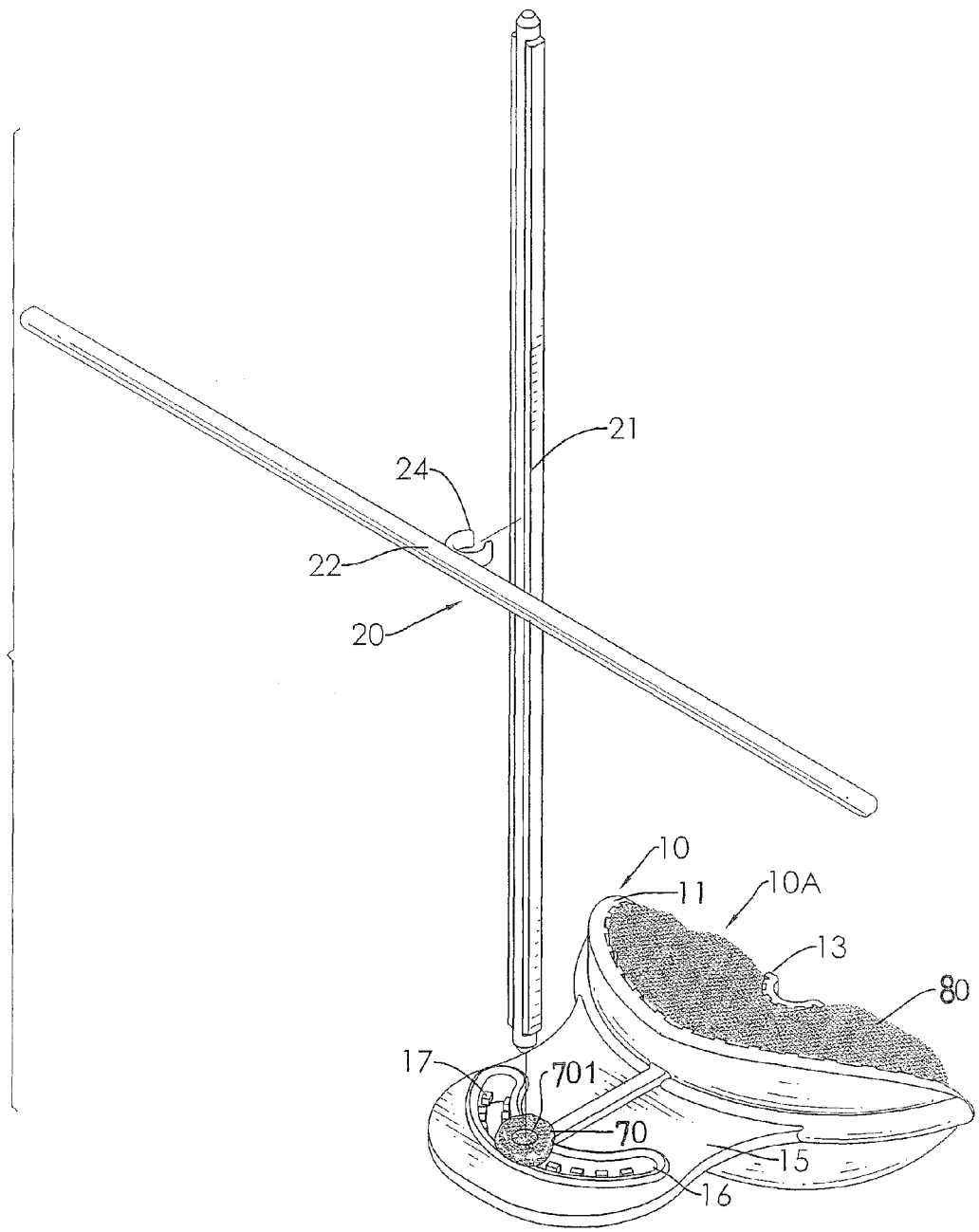
FIG. 5 is an operational perspective view of the dental impression tray in FIG. 1 after loading with silicone rubber and immediately before insertion into the patient's mouth.

With reference to FIGS. 1 and 5, a dental impression tray in accordance with the present invention has a base (10) and a relator (20).

The base (10) has a biting portion (10A) and a handle (15).

Figure 1A:
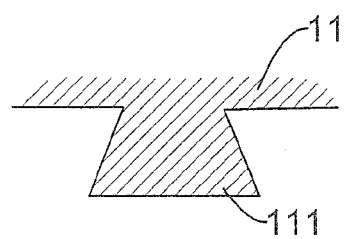
FIG. 1A is a cross sectional top view of a groove in an outer wall of the dental impression tray in FIG. 1.
Figure 1B:
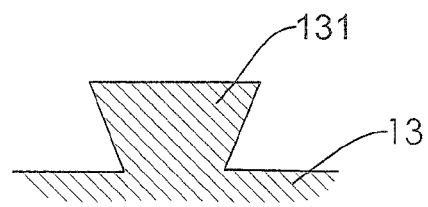
FIG. 1B is a cross sectional top view of a groove in an inner wall of the dental impression tray in FIG. 1.

The biting portion (10A) is curved, corresponds to a human dentition and has an outer wall (11), an inner wall (13) and a membrane (12). The outer wall (11) has a top, a middle part, a bottom, an outer surface, an inner surface and multiple grooves (111). The grooves (111) are formed in the inner surface of the outer wall (11) from the top to the bottom at intervals. Each groove (111) may be flared, which is gradually narrowed from the top and the bottom to the middle part. With further reference to FIG. 1A, each groove (111) is gradually narrowed outward. The inner wall (13) has a top, a bottom, a middle part, an outer surface and multiple grooves (131). The grooves (131) are formed in the outer surface of the inner wall (13) from the top to the bottom at intervals. With further reference to FIG. 1B, each groove (131) is gradually narrowed outward. Each groove (131) may be flared, which is gradually narrowed from the top and the bottom to the middle part. The membrane (12) is formed between the outer wall (11) and the inner wall (13), connects the middle parts of the outer wall (11) and the inner wall (13), is made up of meshes and is able to hold an impression material such as silicon rubber or the like, which, once set, is securely held in the grooves (131). The grooves (131) help to hold the impression material onto the base (10) while the set impression material is removed from the patient's mouth. The handle (15) is formed on the biting portion (10A), may be on the outer surface of the outer wall (11) opposite to the inner wall (13) to allow the impression tray to be held. The handle (15) has an arc hole (16). The arc hole (16) is defined through the handle (15) to receive impression material (70), and has an inner sidewall and multiple protrusions (17). The inner sidewall has a rear sidewall and a front sidewall. The rear sidewall is adjacent to the base (10). The front sidewall is opposite the rear sidewall. The protrusions (17) protrude from the inner sidewall and may be two sets of protrusions (17) protrude respectively from the rear sidewall and the front sidewall at intervals. Preferably, the protrusions (17) on the rear sidewall protrude toward the intervals between the protrusions (17) on the front sidewall and vice versa. The protrusions help to retain the impression material in the arc hole (16) after setting and during removal of the vertical bar from the arc hole.

Figure 3:
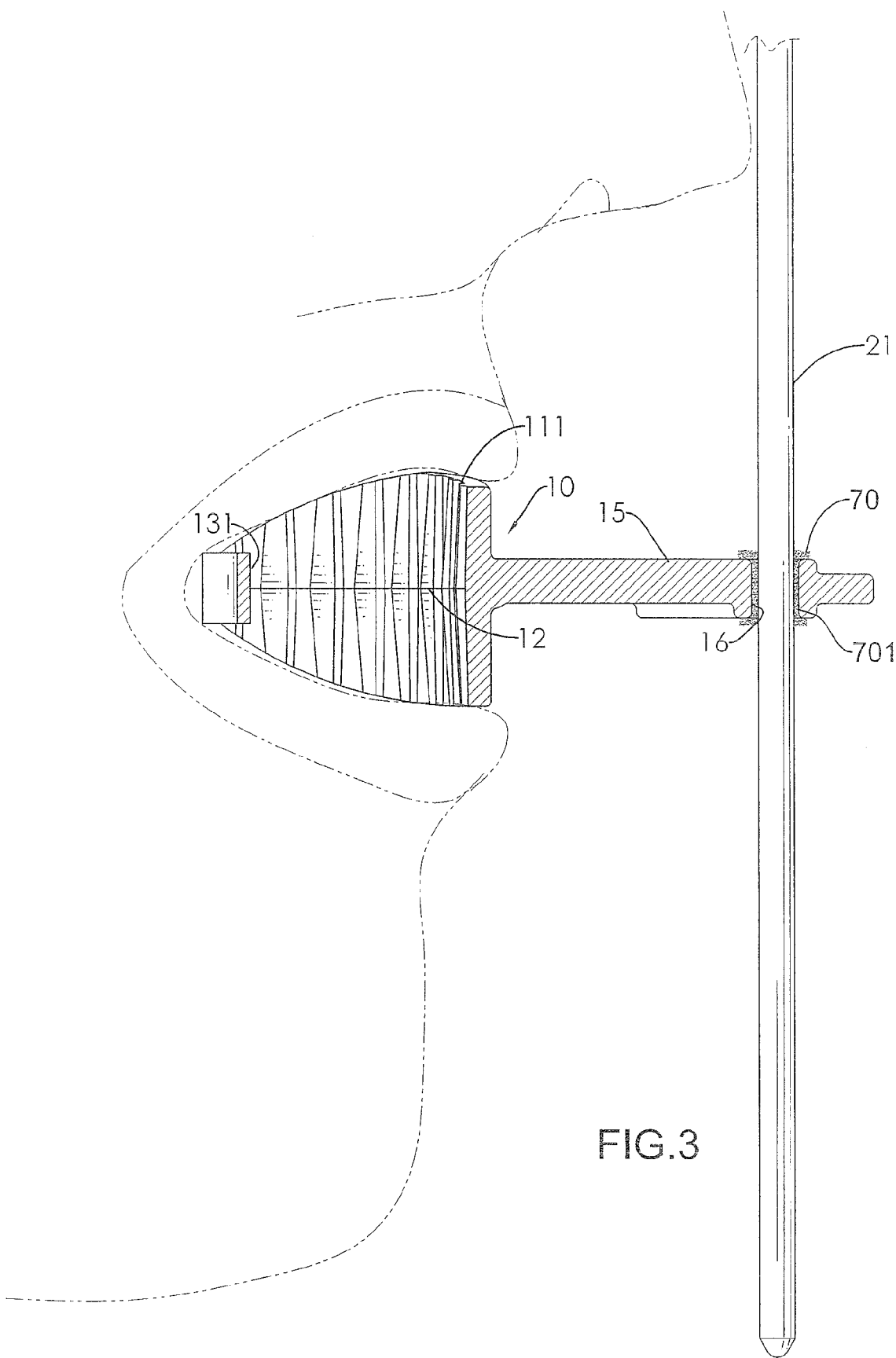
FIG. 3 is an operational side view in partial section of the patient biting into the impression tray and a vertical bar fastened to the body of the dental impression tray in FIG. 1.

With further reference to FIG. 3, the relator (20) comprises a vertical bar (21) and a horizontal bar (22). The vertical bar (21) may be a longitudinal bar, is detachably mounted in the arc hole (16) using impression material (70) to form an alignment hole (701). The horizontal bar (22) may be a longitudinal bar, is attached substantially perpendicularly to the vertical bar (21). The horizontal bar (22) has a clamp (24) for convenient attachment to the vertical bar (21). The clamp (24) may be C-shaped.

The impression material may be any one of the silicone-based rubber-like materials.

A package of the dental impression tray of the present invention before being broken down for use is illustrated in FIG. 1, in which the vertical bar (21) and the horizontal bar (22) are connected horizontally to the handle (15) using bosses (23) that are formed respectively between the vertical bar (21) and the handle (15) and between the vertical bar (21) and the horizontal bar (22). When preparing to use the dental impression tray, the relator (20) is twisted to detach it from the handle (15) and the horizontal bar (22) is twisted relative to the vertical bar (21) to separate the vertical bar (21) and the horizontal bar (22).

Figure 6:
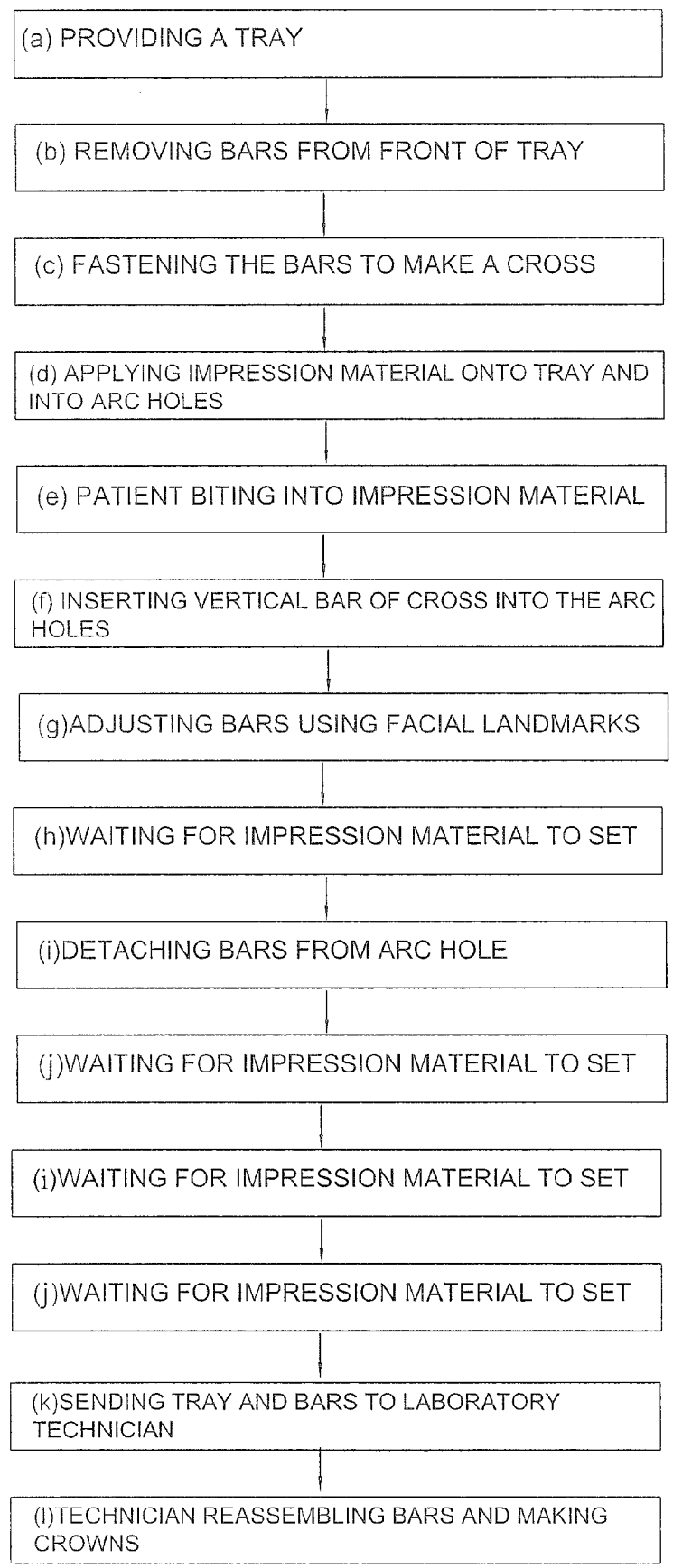
FIG. 6 is a flow diagram of using the dental impression tray in accordance with the present invention.
Figure 7A:
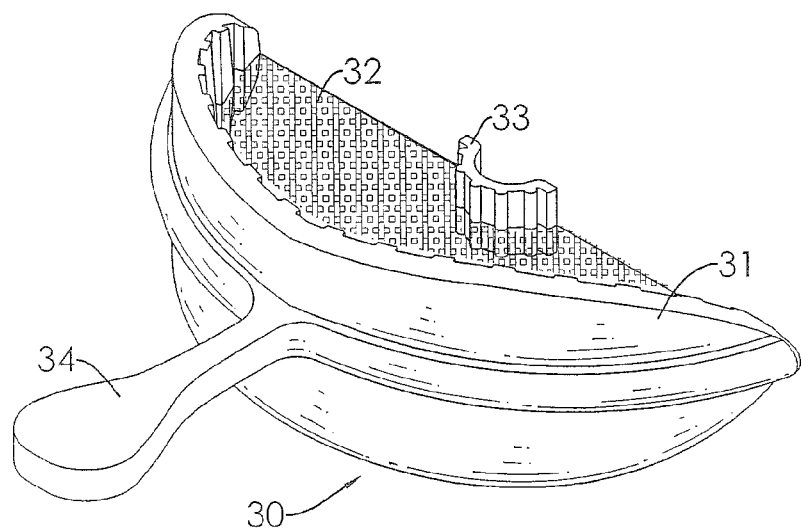
FIG. 7A is a perspective view of a conventional dental impression tray in accordance with the prior art.
Figure 7B:
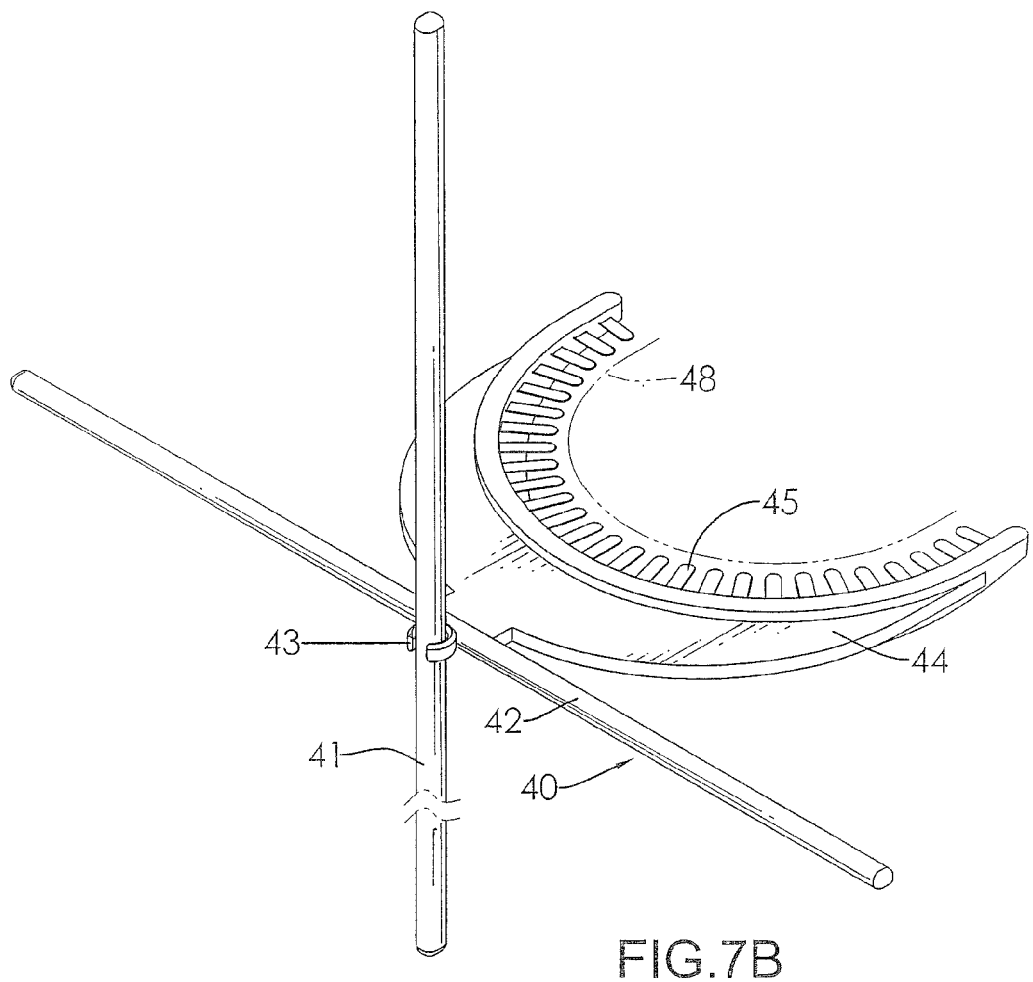
FIG. 7B is a perspective view of a conventional facial plane relator (FPR) in accordance with the prior art.
Figure 8:
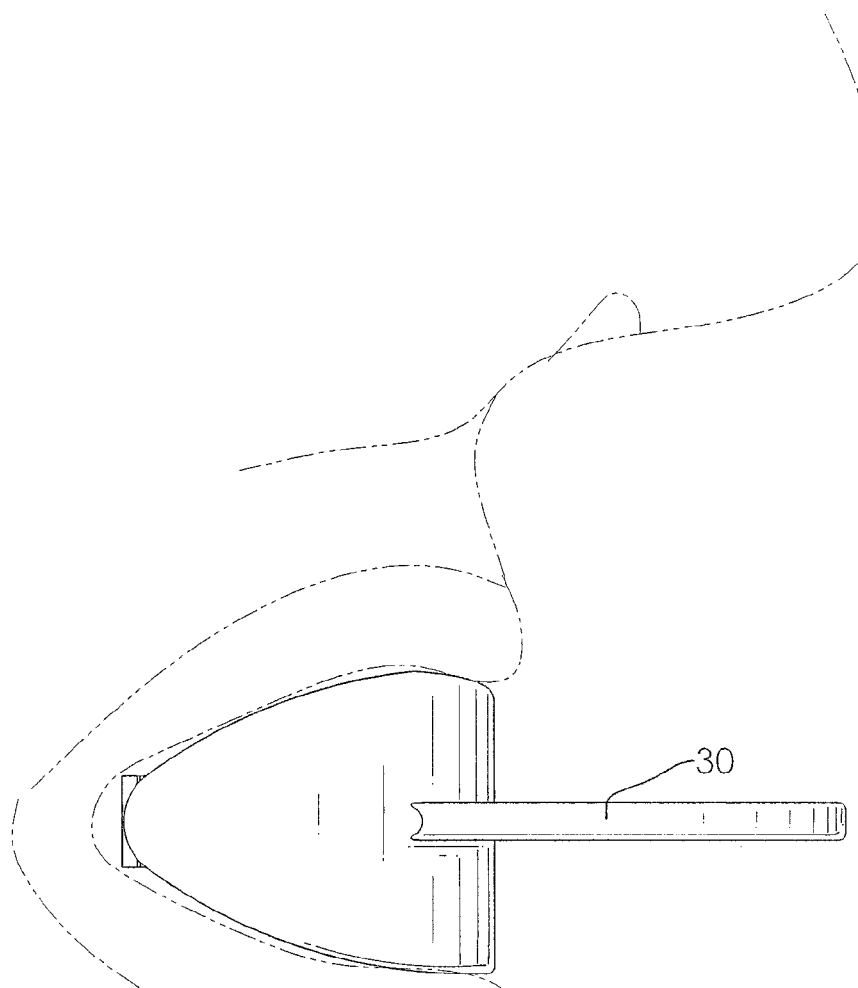
FIG. 8 is an operational side view of a patient biting the conventional dental impression tray in FIG. 7A.
Figure 9:
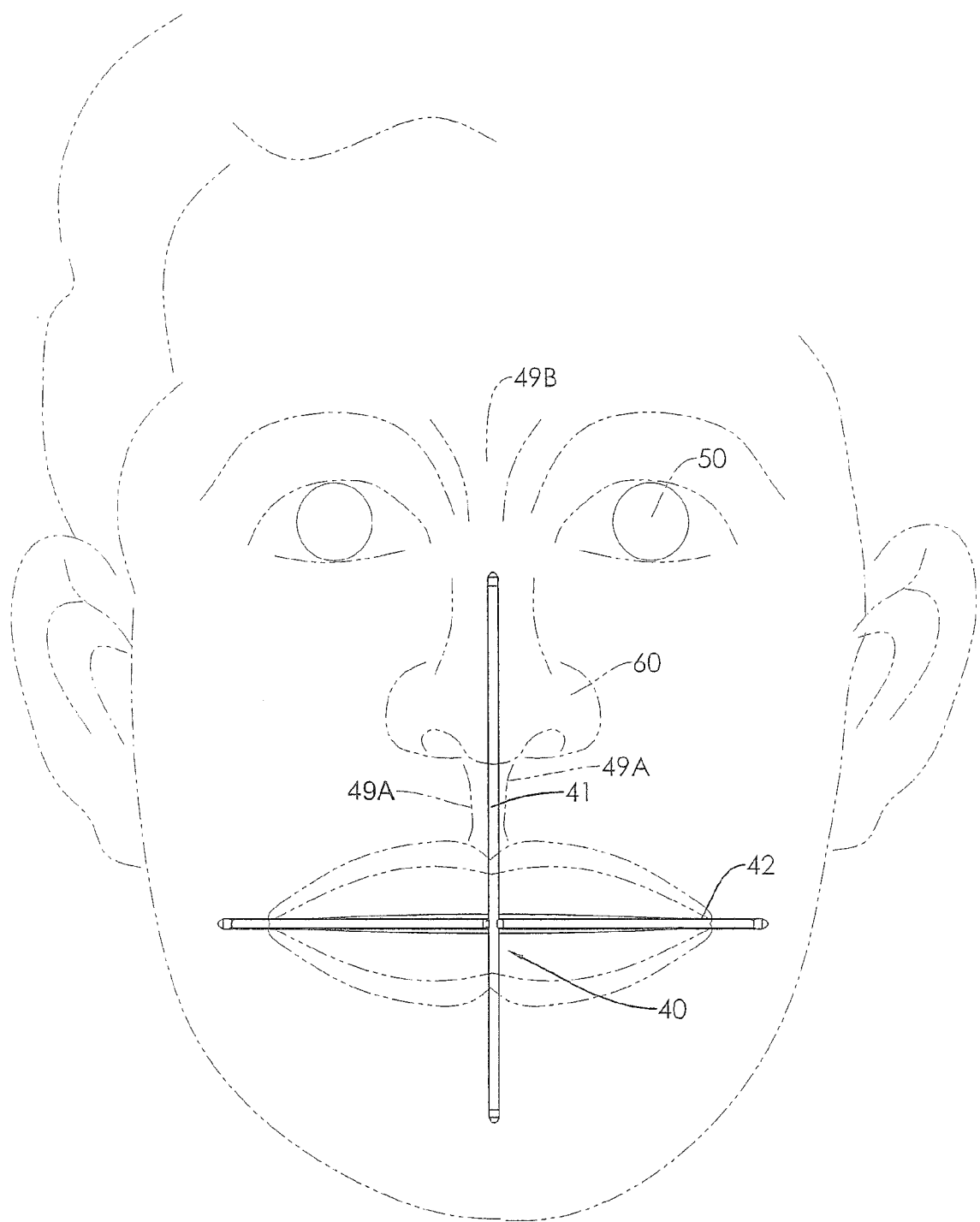
FIG. 9 is an operational front view of a patient biting the conventional FPR in FIG. 7B.
Figure 10:
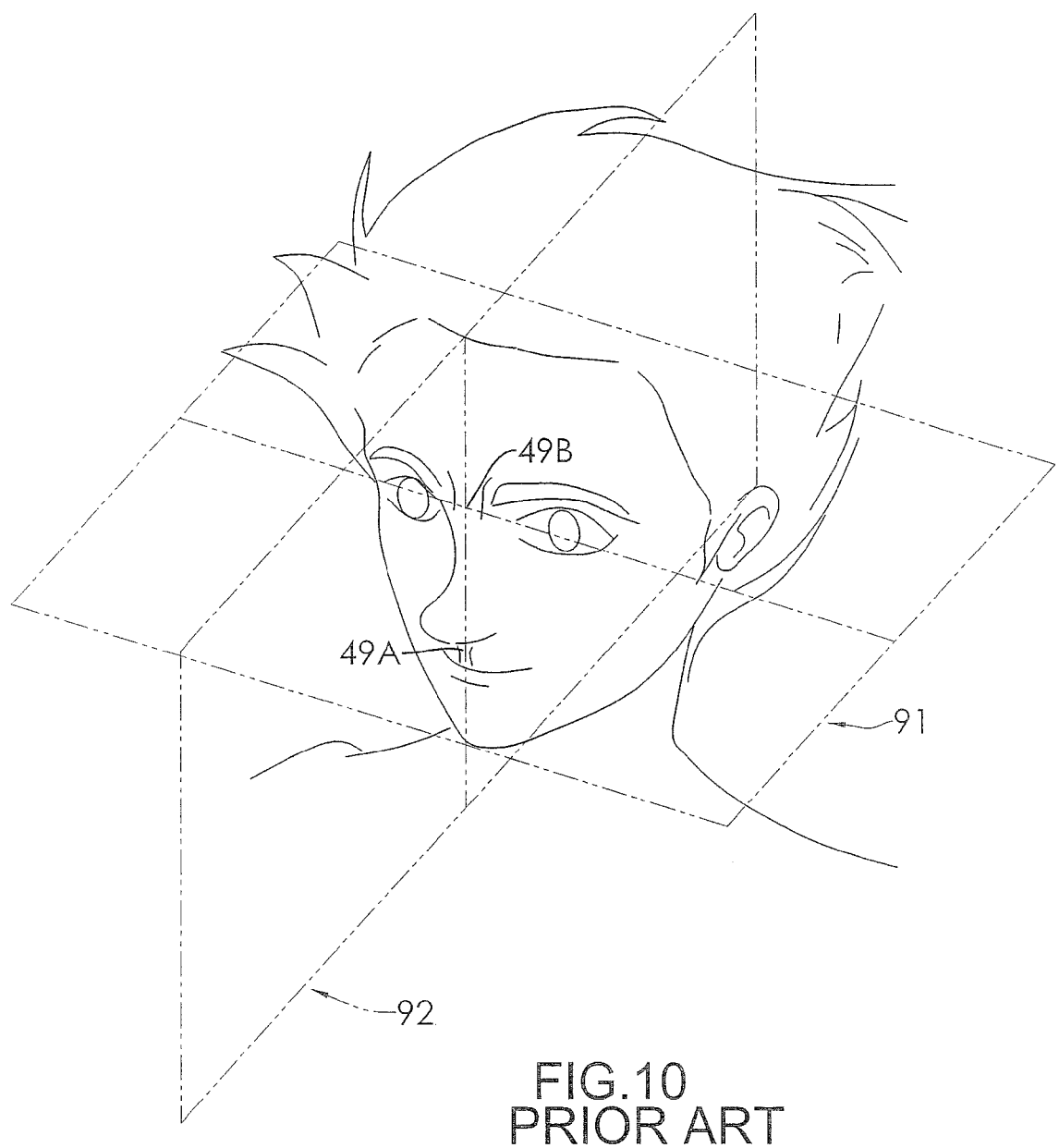
FIG. 10 is a perspective view of a patient's head with horizontal and vertical facial midlines and the planes that traverses through them.
Figure 11:
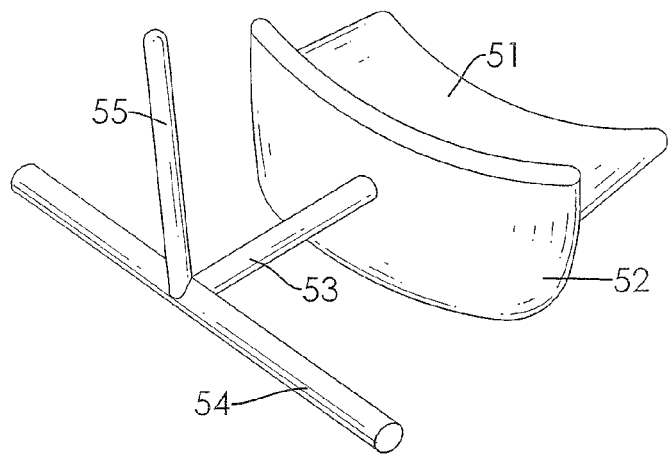
FIG. 11 is a perspective view of another conventional FPR in accordance with the prior art.

With further reference to FIG. 6, the present invention provides a method of using the dental impression tray. The method comprises acts of: (a) providing a tray; (b) removing bars from front of tray; (c) fastening the bars to make a cross; (d) applying impression material onto tray and into arc holes; (e) patient biting into impression material; (f) inserting vertical bar of cross into the arc holes; (g) adjusting bars using facial landmarks; (h) waiting for impression material to set; (i) detaching bars from arc hole; (j) removing tray from mouth; (k) sending tray and bars to laboratory technician; (l) technician reassembling bars and making crowns.

The act of (d) applying impression material comprises selecting and providing appropriate impression material (80) and applying the same to the biting portion (10A) of the base (10) on the membrane (12) between the outer wall (11) and the inner wall (13) as well as applying it into the arc hole (16).

Figure 2:
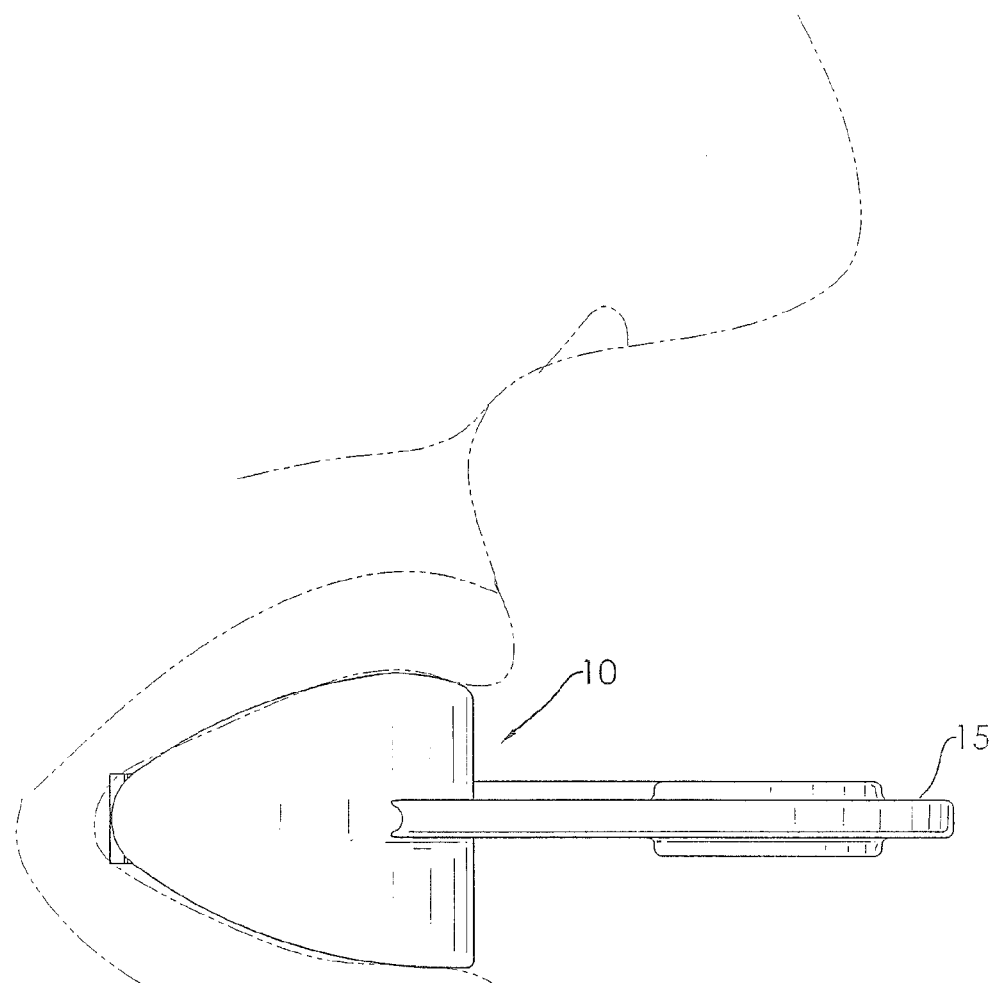
FIG. 2 is an operational side view of a patient biting into the dental impression tray in FIG. 1.

With further reference to FIG. 2, the act of (e) patient biting into impression material comprises putting the biting portion (10A) into a mouth cavity so that the biting portion (10A) is bitten to obtain an impression.

With further reference to FIG. 3, the act of (f) inserting the vertical bar (21) comprises inserting the vertical bar (21) into the material (70), which is held in place by the protrusions (17, not shown in FIG. 3).

Figure 4:
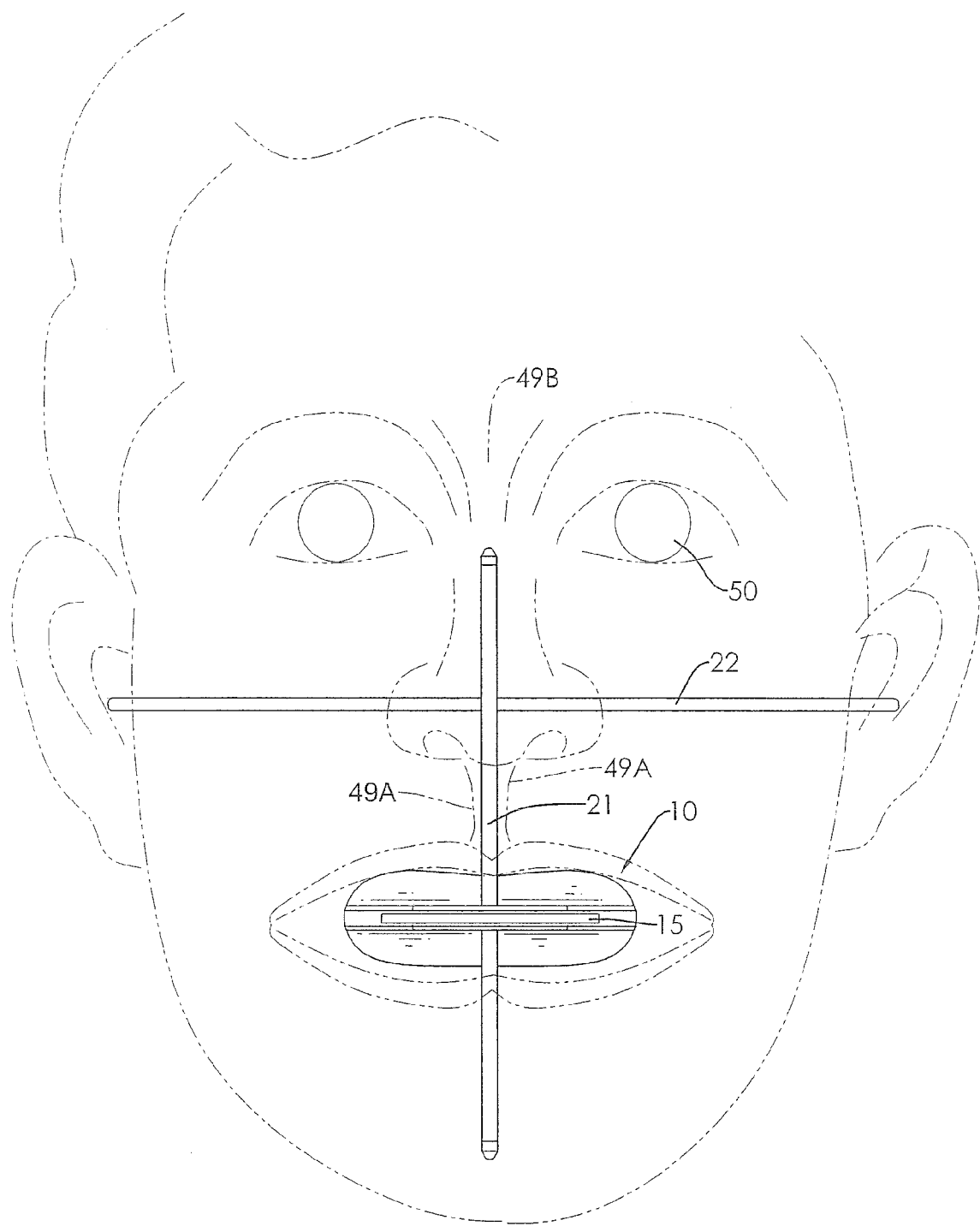
FIG. 4 is an operational front view of a patient biting the dental impression tray in FIG. 1.

With further reference to FIG. 4, the act of (g) adjusting the bar comprises attaching the horizontal bar (22) to the vertical bar (21) via the clamp (24) located on the horizontal bar (22) and aligning the vertical bar (21) with the bridge of the nose (49B) and philtrum (49A) and the horizontal bar (22) with the eyes (50).

The act of (h) waiting for impression material (70, 80) to set comprises allowing the impression material (70, 80) to set.

The act of (i) detaching the bars comprises detaching the vertical bar (21) from the set impression material (70) in the arc hole (16) of the handle (15) to leave an alignment hole (701).

The act of (j) removing the tray comprises removing the biting portion (10A) from the mouth cavity to obtain the impression for producing crowns.

Sequences of the acts of (i) and (j) may be exchanged.

The act of (l) technician reassembling the bars comprises the technician reinserting the vertical bar (21) of the relator (20) into the alignment hole (701) exactly as it was in the patient's mouth.

Accordingly, the impression and the relation between the impression and the patient's face are obtained simultaneously. The horizontal bar (22) can be adjusted along the vertical bar (21) to be close the eyes (50), so the horizontal bar (22) is aligned with the eyes (50) accurately. Furthermore, the relator (20) and the base (10) are able to be detached from each other after the alignment hole (701) is formed and are able to be reassembled after transportation. Therefore, the dental impression tray of the present invention is convenient for dentists and dental technicians to use for improved accuracy and results as well as ease of transport via mail.

Even though numerous characteristics and advantages of the present invention have been set forth in the foregoing description, together with details of the structure and function of the invention, the disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A method of using a dental impression tray comprising:
   providing a tray, the tray comprising
   a base having
      a biting portion being curved; and
      a handle being formed on the biting portion and having an arc hole being defined through the handle to receive an impression material; and
   a relator having
      a vertical bar being detachably mounted in the arc hole using the impression material and forming an alignment hole; and
      a horizontal bar being attached to the vertical bar;
   applying the impression material to the biting portion of the base as well as the arc hole;
   placing the biting portion into the mouth of a patient so that the patient bites into the impression material causing the biting portion to be bitten;
   inserting the vertical bar into the impression material;
   adjusting the bars comprising aligning the vertical bar with bridge of nose and philtrum and the horizontal bar with the patient's eyes; and
   waiting for the impression materials to set comprising allowing the impression material to set to obtain an impression.

2. The method as claimed in claim 1 further comprising detaching the bars comprising detaching the vertical bar from the alignment hole.

3. The method as claimed in claim 2 further comprising reassembling the bars comprising reinserting the vertical bar into the alignment hole.

\* \* \* \* \*